United States Patent [19]

Takeuchi et al.

[11] 4,012,840
[45] Mar. 22, 1977

[54] ADHESIVE PIT AND FISSURE SEALANT

[76] Inventors: Mitsuharu Takeuchi, No. 26-19, 2-chome, Ichikawa, Ichikawa, Chiba; Akira Otsuki, 833-22, Umadateba, Arakawaoki-cho, Tasuchiura, Ibaragi, both of Japan

[22] Filed: Feb. 12, 1976

[21] Appl. No.: 657,585

Related U.S. Application Data

[62] Division of Ser. No. 508,733, Sept. 24, 1974, abandoned.

[52] U.S. Cl. .................................................. 32/15
[51] Int. Cl.² ........................................ A61K 5/02
[58] Field of Search ........................................ 32/15

[56] References Cited

UNITED STATES PATENTS

| | | |
|---|---|---|
| 3,518,762 | 7/1970 | Takeuchi ................................ 32/15 |
| 3,540,126 | 11/1970 | Chang .................................... 32/15 |

*Primary Examiner*—Robert Peshock
*Attorney, Agent, or Firm*—Oblon, Fisher, Spivak, McClelland & Maier

[57] ABSTRACT

An adhesive pit and fissure sealant for tooth surfaces which consists of a first material of a lower alkyl α-cyanoacrylate and ultra-microfine particles of silicon dioxide, a second material of a di-lower-alkylformamide and a third material of a hardening promoter.

1 Claim, No Drawings

ADHESIVE PIT AND FISSURE SEALANT

This is a division of application Ser. No. 508,733 filed Sept. 24, 1974 and now abandoned.

BACKGROUND OF THE INVENTION

1. Field of the Invention

The present invention relates to an adhesive pit and fissure sealant useful in dental practice. More particularly, the present invention relates to an adhesive pit and fissure sealant which is useful in the sealing of pits and fissures of sound teeth to prevent teeth from decaying, and to a method for sealing the same.

2. Description of the Prior Art

The occlusal surfaces of molars have pits and fissures. Food debris and the like penetrate the pits and fissures which eventually results in dental caries. Recently, attempts have been made to seal pits and fissures for the purpose of preventing dental caries.

In an attempt to achieve this purpose Takeuchi et al developed a process to protect sound teeth by coating the teeth with a lower alkyl α-cyanoacrylate over the openings of the pits and fissures. The powder containing PMMA as a base is added thereto and pressed into the pits and fissures which protects the sound teeth (Japanese Pat. No. 689,555). M. G. Buonocore et al have developed a process which comprises etching the surface of teeth with acid and then covering the etched surface with a mixture previously formed from methyl cyanoacrylate and PMMA powder (Journal of the American Dental Association 75, 121, 1967). M. G. Buonocore also developed a sealant consisting of as major ingredients, three parts by weight of the reaction product of bisphenol A and glycidyl methacrylate and one part by weight of methyl methacrylate monomer in which approximately 2% benzoin methyl ester is dissolved as an ultraviolet light sensitive catalyst (Journal of the American Dental Association, 80, 324, 1970). Further, Takeuchi et al have found a tooth filling material useful for sealing cracks, fissures and cavities consisting of a monomeric lower alkyl α-cyanoacrylate, such as ethyl α-cyanoacrylate monomer. The monomer is applied to the tooth followed by a second material comprising microfine particles of a dentally acceptable solid material having a particle size of about 3 to 500 microns, which particles may be in admixture coated with lower alkyl methacrylate polymer, such as methacrylate polymer powder. The dentally acceptable solid materials include gold, silver, nickel, tin, aluminum, platinum, indium, copper, iron, chromium, stainless steel, brass, indium-silver alloy, porcelain and fibrous or powdery glass (U.S. Pat. No. 3,518,762).

As reported by the Committee of the American Dental Association and the Scientific Group of WHO, tooth sealants require simple procedures and short practice times as well as long supporting times. Viewed in this light, the sealing procedure which employs sealants made by Buonocore is complicated and requires long hardening times, i.e., more than 30 seconds. Also, the sealants disclosed in Takeuchi's U.S. patent have the disadvantage that adhesion is decreased even when applied to teeth etched with acid.

A need, therefore, continues to exist for a method of treating dental pits and fissures with a sealing composition by simple procedures and in short practice times.

SUMMARY OF THE INVENTION

Accordingly, one object of the present invention is to provide a new and improved sealant for sealing pits and fissures of sound teeth.

Another object of the present invention is to provide a method for sealing the pits and fissures of sound teeth.

Briefly, these objects and other objects of the invention as hereinafter will become more readily apparent can be attained by an adhesive pit and fissure sealant which consists of a first material of a lower alkyl α-cyanoacrylate and ultra microfine particles of silicon dioxide, a second material of a di-lower alkylformamide and a third material of a hardening promoter.

DETAILED DESCRIPTION OF THE PREFERRED EMBODIMENTS

The first material used in the composition of the present invention is a lower alkyl α-cyanoacrylate, e.g., methyl, ethyl, n-propyl, isopropyl, n-butyl and isobutyl α-cyanoacrylates. Of these, ethyl α-cyanoacrylate is particularly preferred.

The first material also contains ultra microfine particles of silicon dioxide which are available as, for example, Aerosil (Nippon Aerosil, trademark) or white carbon. The size of the ultra microfine particles range from 10 to 100 millimicrons and hydrophobic particles are particularly preferred. The sizes of the silicon dioxide particles are one thousandth to one ten thousandth of the particle size of the fillers hitherto used in the dental field. The smaller size particles result in favorable properties of the sealing material as mentioned below by mixing 1 to 30% by weight, preferably 5 to 10% by weight of the lower alkyl α-cyanoacrylate.

The first material formulated possesses thixotropy, and flows and spreads by applying power to the surfaces of the teeth even after the second material is added to initiate polymerization. The first material is very important in obtaining the improved results of the present invention.

When the silicon dioxide which is hydrophobic is combined with the lower alkyl α-cyanoacrylate, the hydrophilic properties of the resulting sealing material are substantially reduced, which increases the water-resisting qualities in oral cavities and prevents the deterioration of teeth. Favorable properties, such as the hardness and abrasion-resistant properties, are reinforced with silicon dioxide.

Because the ultra microfine particles are uniformly dispersed, the material is useful in reducing the residual strain of the resin on hardening and decreases the thermal expansion coefficient in the oral cavities after sealing and thereby relieves the influence of the internal stress of the sealing material. Accordingly, exfoliation, loss or leakage of the sealing material does not occur, and the adhesive strength to the teeth is maintained semipermanently. In the prior art compositions when the filler having a large particle size is combined with the resin in the sealing material, the abrasion-resistant properties were improved but the resinous properties were spoiled. This disadvantage is improved in the present invention.

The second material used in this invention is a di-lower alkyl formamide, which may be employed in admixture with the first material just prior to use to initiate polymerization of the lower alkyl α-cyanoacrylate. One to 20 parts, preferably 2 to 10 parts by weight of the di-loweralkyl formamide per 100 parts by weight of the first material is mixed with the first material. The thus obtained mixture may be employed within 2 to 3 minutes to 1 to 2 hours after mixing, which time may be controlled according to the amount of di-lower-alkyl formamide in the admixture. The polymerization rate may be regulated by adding a very small amount of water to the di-loweralkylformamide or by blowing carbon dioxide into the di-loweralkylformamide.

Di-loweralkylformamide acts as a catalyst in the anionic polymerization reaction of lower alkyl α-cyanoacrylate, which progresses slowly. In such slow polymerization, a polymer having a high degree of polymerization is obtained, which has lowered residual strain and elevated flexibility in comparison with polymers obtained by rapid polymerization. Although the shrinkage coefficient of the lower alkyl α-cyanoacrylate on polymerization is, in general, large, the influence of shrinkage after sealing is decreased in the present invention as contraction, which will occur on polymerization, is produced before sealing by adding a di-loweralkylformamide to the first material prior to sealing to initiate the polymerization. As a result, the sealing of pits and fissures in the teeth, and the adhesive strength between the sealing material and tooth were found to be stable, and the integrity of the seal is maintained for a long time.

The third material of this invention includes N,N-dimethyl-p-toluidine, N,N-dimethylaniline and N,N-diethylaniline, which are generally dissolved in ethanol, n-hexane or the like.

Preferably, the surfaces of the teeth to be treated are prepared by brushing with pumice, etching with acids such as phosphoric acid and citric acid, washing with water and air-dried.

In performing the sealing technique of the present invention using the described materials, the mixture of the first and second materials which begins to polymerize, is coated on the surfaces of the teeth pretreated as described above, with the tip of a small brush. Since the mixture of materials is thixotropic as mentioned earlier in spite of its high viscosity, homogeneous coating of the desired portions is possible and clinical processability is very excellent.

Immediately after the first and second materials are mixed, the teeth are covered with the mixture. The third material is then applied. Hardening of the surface of the sealing material occurs within 10 to 15 seconds and occlusion is made possible. However, in the inner portions of the sealing material, the polymerization proceeds slowly because of the presence of the di-loweralkylformamide and thereby the preferred polymer is obtained. The results obtained are excellent and the tooth surfaces are finely finished. Grinding of the occlusal surfaces is not required, except when the sealing is too high.

The coated sealant adheres firmly to teeth physically and chemically at the surfaces of the pits and fissures, and does not easily exfoliate, loosen or leak out.

Having generally described this invention, a further understanding can be obtained by reference to certain specific examples which are provided herein for purposes of illustration only and are not intended to be limiting unless otherwise specified.

EXAMINATION 1

Percolation test

After the pits and fissures of extracted human molar teeth were sealed according to the present process, they were exposed to severe conditions and were immersed alternately in 0.2% fuchsin aqueous solution at 4° C and 60° C, respectively for one minute. This procedure was repeated for 3 hours, and the teeth were tested.

As a result of the examination, it was found that no pigments penetrated the joining interfaces between the sealant and teeth, and the sealant was not stained at all. These results indicated that the sealant according to the present invention completely adhered to the teeth and exhibited good durability over a long time in oral cavities.

EXAMINATION 2

Tensile adhesive strength test

The adhesive strength of sealant to the enamel of teeth was tested in the following manner. After the labial surface of a bovine tooth was etched with acid, the tooth was coated with a mixture of the first and second materials of the sealant of the present invention. A round stick of Polymethacryl (6 mm diameter) was placed against the coated materials and the third material was applied onto the surface of the materials to harden the composition.

The coated tooth was immersed in water at 37° C for one week within 5 minutes after applying the third material, and thereafter the tensile strength was measured with a tensile testing machine and the adhesive strength per unit of area was calculated.

| Sealants of this invention | | Adhesive strength |
|---|---|---|
| Ethyl α-cyanoacrylate | 100 parts | |
| Aerosil R 972 | 10 parts | $110 \pm 20$ Kg/cm$^2$ |
| Dimethylformamide | 5 parts | |
| n-Hexane solution containing 2% of N,N-dimethyl-p-toluidine | | |
| Ethyl α-cyanoacrylate | 100 parts | |
| Aerosil R 972 | 5 parts | $145 \pm 30$ Kg/cm$^2$ |
| Dimethylformamide | 5 parts | |
| n-Hexane solution containing 2% of N,N-dimethyl-p-toluidine | | |
| Ethyl α-cyanoacrylate | 100 parts | |
| Aerosil OX 50 | 10 parts | $133 \pm 26$ Kg/cm$^2$ |
| Dimethylformamide | 5 parts | |
| n-Hexane solution containing 2% of N,N-dimethyl-p-toluidine | | |

As can be seen from these results, the sealant of this invention adheres extremely well compared to the conventional sealants.

As mentioned above, the processability, water-resisting properties and the hardness of the composition of the present invention are improved by employing the combination of the first, second and third materials. Moreover, sealants having lowered residual strain and great flexibility are obtained as shrinkage on hardening is reduced and internal stress is relieved because of the combination of an ultra-microfine powder of silicon dioxide and the slow starting of the polymerization caused by the di-loweralkylformamide. Thus, great adhesive strength between the sealants and the enamel is maintained.

EXAMPLE

The first material: 7 percent Aerosil R 972 is mixed with ethyl α-cyanoacrylate.

The second material: Dimethylformamide.

The third material: n-Hexane solution containing 2%, N,N-dimethyl-p-toluidine.

Five percent of the second material was mixed with the first material as described above and then the resulting mixture was allowed to stand for 2 to 10 minutes, during which time the surfaces of the molar teeth of a patient were etched with 3 M phosphoric acid for 30 seconds, and washed with water. Moisture was removed from the teeth by a cotton roll and the teeth were air-dried. The mixture of the first and second materials as described above was coated onto the teeth surfaces by the tip of a small brush impregnated with the mixture. The mixture penetrated into the pits and fissures of the teeth. Then the third material was applied onto the teeth surfaces and allowed to stand for 5 to 15 seconds. It took about 2 minutes to treat the patient.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for preventing teeth from decaying by sealing pits and fissures of sound teeth, which comprises:

coating the surface of teeth with a mixture of a first material comprising a lower alkyl α-cyanoacrylate and ultra-microfine particles of silicon dioxide and a second material comprising a di-loweralkylformamide and then applying a third material of N,N-dimethyl-p-toluidine, N,N-dimethylaniline or N,N-diethylaniline onto the coated surface.

* * * * *